(12) United States Patent
Gracey

(10) Patent No.: US 6,403,839 B1
(45) Date of Patent: Jun. 11, 2002

(54) PROCESS FOR MAKING BUTYRALDEHYDE FROM BUTADIENE

(75) Inventor: Benjamin Patrick Gracey, Hull (GB)

(73) Assignee: BP Chemicals Limited, London (GB)

( * ) Notice: Subject to any disclaimer, the term of this patent is extended or adjusted under 35 U.S.C. 154(b) by 0 days.

(21) Appl. No.: 09/878,313

(22) Filed: Jun. 12, 2001

Related U.S. Application Data

(63) Continuation of application No. PCT/GB99/04171, filed on Dec. 10, 1999.

(30) Foreign Application Priority Data

Dec. 22, 1998 (GB) .............................................. 9828338

(51) Int. Cl.[7] .............................................. C07C 47/02
(52) U.S. Cl. ........................ 568/484; 568/449; 568/450
(58) Field of Search ................................ 568/449, 450, 568/484

(56) References Cited

U.S. PATENT DOCUMENTS

| 3,391,192 A | | 7/1968 | Zuech et al. | |
|---|---|---|---|---|
| 5,705,707 A | * | 1/1998 | Kanand et al. | ............. 568/487 |
| 5,892,125 A | * | 4/1999 | Kanand et al. | ............. 568/449 |

FOREIGN PATENT DOCUMENTS

| WO | 95/19334 | 7/1995 |
|---|---|---|
| WO | 96/07630 | 3/1996 |
| WO | 98/41494 | 9/1998 |

* cited by examiner

*Primary Examiner*—Sreeni Padmanabhan
(74) *Attorney, Agent, or Firm*—Nixon & Vanderhye

(57) ABSTRACT

Process for making butyraldehyde from an n-butenyl ester of a carboxylic acid, wherein the n-butenyl ester is hydrolyzed to form the corresponding n-butenyl alcohol n-butenyl alcohol so produced is isomerized to form butyraldehyde.

17 Claims, No Drawings

PROCESS FOR MAKING BUTYRALDEHYDE FROM BUTADIENE

This is a continuation of PCT/GB99/04171 filed Dec. 10, 1999.

The present invention relates to a process for making butyraldehyde by hydrolysing an n-butenyl ester to form the corresponding n-butenyl alcohol and isomerising the latter to form butyraldehyde.

It is known that butyraldehyde can be produced by a number of routes. For instance, U.S. Pat. No. 5,705,707 discloses a method of making n-butyraldehyde and/or n-butanol by reacting butadiene with an alcohol in the presence of an acidic catalyst. The reaction produces a mixture of isomeric adducts, 1-alkoxybutene-2 (a) (also known as crotyl ether) and 3-alkoxybutene-1 (b):

　(a)

　(b)

Compound (b) can be isomerised into compound (a). Compound (a) is isomerised in the presence of a homogeneous or heterogeneous transition metal catalyst to form the enol ether of the formula (c):

　(c)

Ether (c) reacts with water to liberate butyraldehyde. This hydrolysis reaction is catalysed by acids and bases. The butyraldehyde product can be hydrogenated with suitable homogeneous or heterogeneous catalysts to yield n-butanol. Thus compound (c) in the presence of water and hydrogen and a homogeneous or heterogeneous catalyst produces butanol and the parent alcohol ROH. The parent alcohol can then be recycled to the addition reaction stage.

A similar isomerisation hydrolysis reaction has been repeated with amines in DE-A-4431528. This document describes a process for the production of butyraldehyde which comprises the addition of an amine to a butadiene. The reaction produces a mixture of isomers, $CH_3CH{=}CHCH_2NR_2$ and $CH_3CH(NR_2)CH{=}CH_2$. The $CH_3CH(NR_2)CH{=}CH_2$ isomer is recycled back to the addition reaction, whilst the $CH_3CH{=}CHCH_2NR_2$ isomer is converted to the corresponding enamine, $CH_3CH_2CH{=}CHNR_2$. This enamine is hydrolysed to produce butyraldehyde for possible further processing and also liberates the initial amine for re-use. The butyraldehyde may be hydrogenated to the corresponding alcohol, if desired. The process of DE-A-4431528 is summarised in the diagram below:

The selectivity of the above processes has been found to be limited by the formation of by-products. Such by-products include C8 and higher species formed, for example, by dimerisation and oligomerisation reactions of C4 species. In the process of DE-A-4431528, by-products may also be produced by amine catalysed aldol condensation reactions of butyraldehyde.

We have now found that the selectivity of the butyraldehyde production process can be increased by forming butyraldehyde from a butenyl ester.

Accordingly, the present invention provides a process for making butyraldehyde from an n-butenyl ester of a carboxylic acid, said process comprising i) hydrolysing the n-butenyl ester to form the corresponding n-butenyl alcohol and ii) isomerising the n-butenyl alcohol produced in step i) to form butyraldehyde.

By "isomerising" is meant performing any process which results in the direct or indirect conversion of the n-butenyl alcohol to butyraldehyde.

Steps i) and ii) may be carried out simultaneously or sequentially. Whilst carrying out steps i) and ii) simultaneously may allow the process to be operated more economically, the sequential hydrolysis and isomerisation stages may increase the selectivity of the overall process.

Step i) may also be carried out before step ii). Thus, in one embodiment of the present invention, n-butenyl ester is first hydrolysed to form n-butenyl alcohol, which is conveniently separable from the hydrolysis mixture as an azeotrope. The separated n-butenyl alcohol is then isomerised into the butyraldehyde product.

Preferably, the n-butenyl ester is an n-butenyl ester of a saturated, aliphatic carboxylic acid.

In the present process, the n-butenyl ester (also known as "crotyl ester") may not be readily available commercially. Instead it may be produced by reacting butadiene with a saturated, aliphatic carboxylic acid. As butadiene is a relatively inexpensive by-product of the refining process, it provides a convenient feedstock for making butyl esters. Thus, a preferred embodiment of the present invention provides a process for the production of butyraldehyde which comprises:

a) the addition reaction of butadiene to a carboxylic acid to produce a mi)cture of sec-butenyl ester and n-butenyl ester; and
b) (i) hydrolysing the n-butenyl ester formed in step a) to form the corresponding n-butenyl alcohol, and (ii) isomerising of the n-butenyl alcohol produced in step bi) to form butyraldehyde.

Steps (i) and (ii) may be carried out simultaneously or sequentially.

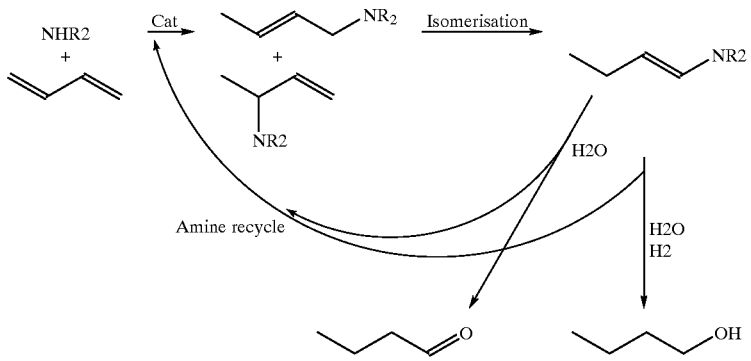

The diagram below summarises the reactions which may take place in this preferred embodiment of the invention.

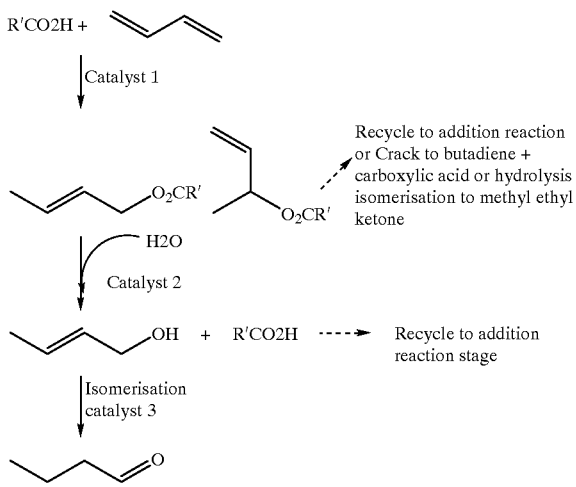

In step a), butadiene is reacted with a carboxylic acid R'CO₂H in the presence of an addition catalyst, catalyst 1. Catalyst 1 may be a homogeneous or heterogeneous catalyst. Heterogeneous catalysts may be advantageous in certain situations as they facilitate separation of, for example, reaction products from the reaction mixture. They may also allow the catalyst to be conveniently separated from reaction by-products (which typically comprise high boiling point butadiene oligomeric species). The preferred catalysts are based on strong acid ion-exchange resins, such as Amberlyst 15® and Amberlite IR120®. Other suitable examples of heterogeneous catalysts include fluorinated ion-exchange resins such as Nafion®, phosphoric acid functionalised polymers, and acidic oxides, for example, HY zeolites.

A proportion of the acidic sites of such ion-exchange catalysts may be exchanged with bulky counterions, such as alkyl pyridinium, quaternary alkyl ammonium, quaternary arsonium and quaternary phosphonium. These counterions exchange with some of the acid sites on the support and can be added to the catalysts as salts, such as halides, sulphates or carboxylates.

The heterogeneous catalyst phase may be a partially or fully insoluble liquid phase. Such catalysts may take the form of acidic ionic liquids, liquid acidic polymers and partially solvated polymers. The catalyst may also be a solid phase, for example, I) an HY zeolite, II) a strong acid macroreticular, macronet or gel ion-exchange resin, or III) a heteropolyacid of tungsten or molybdenum, which has been ion-exchanged and/or supported on a carrier material.

In certain circumstances, the activity of heterogeneous catalysts may decrease considerably after prolonged periods of use. In such cases, it may be advantageous to carry out the process of the present invention in a homogeneous phase. Suitable homogeneous catalysts include sulphonic acids, heteropolyacids, triflic acid (i.e. trifluoromethane sulphonic acid) and triflate salts. Suitable heteropolyacids include Keggin structure heteropolyacids based on tungsten, and strong acid ionic liquids such as those described in prior published EP-A-693088, WO-A-95/21872 and EP-A-558187. Suitable organic sulphonic acids include methane sulphonic acid, p-toluenesulphonic acid and sulphonated calixarenes. Examples of triflate salts include lanthanide triflates, such as lanthanum trifluoromethanesulphonic acid salts.

The presence of water as a reaction adjuvant can also beneficially affect the activity and selectivity of the catalysts. It has been found that moderately low levels of water are required: at levels above 5%w/w the catalyst activity is significantly reduced, whereas at levels below 0.05%w/w, the activity though high is rapidly lost due to deactivation of the catalyst. Consequently the water level in the reaction zone is suitably in the range from 0.05 to 5%w/w on the carboxylic acid, preferably from 0.05 to 1%w/w.

The butadiene feedstock may be employed either as a purified chemical, or in the form of a hydrocarbon stream comprising butadiene. Such hydrocarbon streams include refinery streams such as mixed C4 streams containing butadiene, as well as other C4 species such as butane, 1-butene, 2-butene, isobutane, and isobutene. The addition reaction (step (a)) can be used to remove butadiene from such hydrocarbon streams, thereby avoiding the need to remove butadiene in a separate processing stage.

The butadiene employed may be dissolved in the reaction mixture, or introduced into the reactor as a gaseous reactant. In certain embodiments, the reaction is carried out in multi-phase, with butadiene being present in the liquid reaction mixture, and as a gaseous phase.

The carboxylic acid (RCO₂H) feedstock suitably comprises any saturated carboxylic acid feedstock. Dicarboxylic acids such as succinic acid may be employed, although mono-carboxylic acids, and in particular, aliphatic mono-carboxylic acids are generally preferred. Suitable mono-carboxylic acids comprise 1–6 carbon atoms. Preferably, the acid is acetic acid.

The relative mole ratios of butadiene to the carboxylic acid reactant in the addition reaction is suitably in the range from 5:1 to 1:50, preferably in the range from 1:1 to 1:10.

This addition reaction is suitably carried out at a temperature in the range from 20 to 150° C., preferably from 40 to 90° C. The reaction is suitably carried out at the autogeneous reaction pressure which is determined by factors such as the reaction temperature, presence of absence of solvent, excess of reactants and impurities present in the butadiene stream. An additional pressure may be applied to the system if the reaction is carried out in a single phase, for example, if substantially all the butadiene present is present in the liquid phase in the reaction mixture.

It may also be advantageous to use polymerisation inhibitors such as eg alkylated phenols such as 2,6-di-tert-butyl-p-cresol (also known as "BHT" or butylated hydroxytoluene). Other related compounds include the Irganox® series of materials (ex Ciba Gigy), the Lowinox® series of materials (ex Great Lakes Chemical Corporation); the Tropanol® series (ex ICI), t-butylcatechol, nitroxides such as di-tert-butylnitroxide, N,N-dimethyl-4-nitrosoaniline, nitric oxide, and stable radicals, such as 2,2,6,6-tetramethyl-piperidine-1-oxyl, 2,2,6,6-tetramethyl-4-hydroxypiperidine-1-oxyl and 2,2,6,6-tetramethylpyrrolidine-1-oxyl.

The reaction between butadiene and the carboxylic acid produces a mixture of butenyl esters: n-butenyl ester and sec-butenyl ester. The n-butenyl ester is converted into the butyraldehyde end-product by hydrolysis isomerisation (step (b)). The sec-butenyl ester, on the other hand, may be removed, for example, for use, sale or further reaction. An example of such a further reaction is the conversion of sec-butenyl ester into methyl ethyl ketone and carboxylic acid. Such a conversion step may be carried out by subjecting the ester to simultaneous or sequential stages of hydrolysis and isomerisation. As with the n-butenyl isomer, simultaneous hydrolysis and isomerisation may allow the process to be operated more economically. However, sequential hydrolysis and isomerisation stages may increase the selectivity of the overall process.

Where the hydrolysis and isomerisation steps are carried out sequentially, it is preferable for the sec-butenyl ester to be hydrolysed before it is isomerised. This is because the conversion of the allylic ester to its vinyl isomer has been found to be thermodynamically unfavourable. Thus, in one embodiment of the present invention, sec-butenyl ester is first hydrolysed to form but-l-en-3-ol, which is conveniently separable from the hydrolysis mixture as an azeotrope. The separated alcohol is then isomerised into the ketone product.

Instead of (or in addition to) converting the sec-butenyl ester into methyl ethyl ketone, the sec-butenyl ester may also be recycled back to the addition reaction (step (a)). Under the reaction conditions, sec-butenyl interconverts with butadiene, free carboxylic acid and the n-butenyl ester. Rather than recycling the sec-butenyl ester to the addition reaction directly, however, it is also possible to convert the sec-butenyl ester back into butadiene and carboxylic acid separately. The conversion of the sec-butenyl ester to free carboxylic acid and butadiene can be achieved by treatment in the vapour phase with an acidic support. Suitable supports include silica-aluminas. The butadiene and carboxylic acid produced may then be returned to the addition reactor. This may have a beneficial effect on productivity and selectivity. Alternatively, at least one of the butadiene and carboxylic acid may be sold, or used for further reaction.

The addition reaction may be carried out in a plug flow reactor, with the unused butadiene being flashed off and recycled to the reactor via a vapour liquid separator. Some of the butadiene may be present as a separate gas phase, whilst the remainder of the butadiene is dissolved in the reaction mixture. This results in either a trickle bed or bubble bed operation. A typical LHSV (liquid hourly space velocity=volume of liquid feed /catalyst bed volume) for the carboxylic acid is 0.5 to 20 more preferably 1 to 5.

The addition reactor may alternatively be carried out in a slurry reactor. In such a reactor, the deactivated catalyst may be continuously removed from the reactor as a bleed stream. It is economically advantageous to run with catalyst in various stages of deactivation to improve the utilisation of catalyst. In this case, the total loading of catalyst (activated+ deactivated) can reach high levels such as 50%w/w of the reaction charge.

The butadiene may be added gradually to the carboxylic acid, for example, by multiple injection at constant pressure. This may be carried out in a batch reactor. By adding the butadiene gradually in this manner, side reactions leading to, for example, the polymerisation of the butadiene may be minimized.

The products produced by the addition reaction may be separated from the reactants by distillation. A small amount of water azeotroping of reaction products may occur due to the low levels of water employed. However, this is minor and does not significantly effect the separation of the isomeric butenyl esters, i.e. the n-butenyl ester and secondary butenyl ester.

The n-butenyl ester produced in the addition step is converted to butyraldehyde in step b). This is achieved by i) hydrolysis and ii) isomerisation. Where steps i) and ii) are carried out simultaneously, a transition metal catalyst may be used in the presence of an acid or base to perform the purpose of catalysts 2 and 3 (see diagram). Preferred transition metal complexes are those containing elements from Group Ib, Vb, VIb, VIIb and VIIIb of the Periodic Table of Elements on pages 448 and 449 of the Handbook of Physics & Chemistry (44$^{th}$ Edition) published by the Chemical Rubber Publishing Company, Ohio USA (Reprint, April 1962), particularly copper, vanadium, chromium, molybdenum, tungsten, manganese, rhenium, iron, cobalt, nickel, ruthenium, rhodium, palladium, platinum, osmium and/or iridium. Preferably, a transition metal catalyst supported on an acidic residue is employed. Examples of suitable acidic residues include strongly acidic ion-exchange resins and sulphonic acids such as para-toluene sulphonic acid. Mineral acids such as sulphuric acid and halogen acids; acidic oxides such as HY zeolite; Lewis acids such as lanthanide triflates; and organic acids such as triflic acid may also be suitable. One advantage of carrying out the hydrolysis and isomerisation steps simultaneously is that it minimises the total number of process stages required for the production of the final product. The butyraldehyde produced may be recovered from the reaction mixture by distillation, preferably, whilst the hydrolysis/isomerisation reaction is in process.

The simultaneous hydrolysis and isomerisation step may be carried out in the liquid phase, optionally, in the presence of a solvent such as an aromatic hydrocarbon solvent. Suitable solvents include toluene and ethers, such as methyl tertiary butyl ether and tetrahydrofuran. The reaction may be carried out at a temperature of from 25 to 250° C., preferably, from 50 to 150° C. and more preferably, from 80 to 120° C.

When the hydrolysis and isomerisation steps are carried out sequentially, the hydrolysis step may be carried out in the presence of an acid or a base, such as a Bronsted acid or base (catalyst 2). Suitable isomerisation catalysts (catalyst 3) include transition metal complexes. Preferred transition metal complexes are those containing elements from Group Ib, Vb, VIb, VIIb and VIIIb of the Periodic Table of Elements on pages 448 and 449 of the Handbook of Physics & Chemistry (44$^{th}$ Edition) published by the Chemical Rubber Publishing Company, Ohio USA (Reprint, April 1962), particularly copper, vanadium, chromium, molybdenum, tungsten, manganese, rhenium, iron, cobalt, nickel, ruthenium, rhodium, palladium, platinum, osmium and/or iridium.

The n-butenyl ester, upon hydrolysis, will produce an equilibrium mixture of n-butenyl (i.e. crotyl) alcohol and the carboxylic acid. In order to force the equilibrium in the desired direction it may be necessary to remove the carboxylic acid, or alcohol from the equilibrium mixture. This may be achieved by removing the alcohol as an azeotrope.

The hydrolysis step may be carried out in the liquid phase, optionally, in the presence of a solvent such as an aromatic hydrocarbon solvent. Suitable solvents include toluene and ethers, such as methyl tertiary butyl ether and tetrahydrofuran. The reaction may be carried out at a temperature of from 25 to 250° C., preferably, from 50 to 150° C. and more preferably, from 80 to 120° C. The crotyl alcohol formed as a result of this hydrolysis step may be recovered by distillation or by phase separation into a suitable solvent. This crotyl alcohol is then isomerised in a separate stage to give butyraldehyde.

The present invention is further illustrated, by way of example, with reference to the following examples:

EXAMPLES

The Preparation of Butyraldehyde from Crotyl acetate

The following chemicals were used in the preparation:

Crotyl acetate: 91 g (100 ml, 0.79 mol)

$RuCl_3$: 1 g (0.005 mol)

NaOH: 2.1 g (0.05 mol)

de-ionised water

Under a steady flow of nitrogen as inert gas, crotyl acetate (91.0 g, 100 ml, 0.79 mol) and 100 ml of an aqueous solution of RuCl$_3$ (1 g, 0.005 mol in 50 ml deionised water) were mixed in a three-necked round-bottomed flask equipped with a 15 plate Oldershaw separation column to which a liquid reflux splitter was fitted. A pressure equalising dropping funnel was also connected to the reaction flask. The reaction mixture was stirred and heated to ca. 90° C. and a dropping funnel was used to slowly add aqueous sodium hydroxide solution (2.1 g, 0.05 mol in 100 ml de-ionised water) over a period of 2–3 hours. The temperature at the top of the separation column was constantly monitored and the first distillation fraction of a water/butyraldehyde was collected between 68–72° C. and an additional fraction between 80–82° C. (water/crotyl alcohol). The first fraction contained the major amount of the butyraldehyde product (as determined by GC analysis) and was worked up by separating the water layer from an organic layer comprising butyraldehyde in a separating funnel. The second fraction mainly contained crotyl alcohol. Subsequently, the organic layer containing the desired butyraldehyde product was dried over magnesium sulphate overnight and butyraldehyde was obtained with an estimated yield of 80% (46.8 g, 58.5 ml, 0.632 mol).

I claim:

1. A process for making butyraldehyde from an n-butenyl ester of a carboxylic acid, said process comprising hydrolysing the n-butenyl ester to form the corresponding n-butenyl alcohol and ii) isomerising the n-butenyl alcohol produced in step i) to form butyraldehyde.

2. A process as claimed in claim 1, wherein steps i) and ii) are carried out simultaneously.

3. A process as claimed in claim 1, wherein said steps i) and ii) are carried out simultaneously using a transition metal catalyst in the presence of an acid or base.

4. A process as claimed in claim 1, wherein the transition metal catalyst contains at least one of copper, vanadium, chromium, molybdenum, tungsten, manganese, rhenium, iron, cobalt, nickel, ruthenium, rhodium, palladium, platinum, osmium and iridium.

5. A process as claimed in claim 1, wherein said steps i) and ii) are carried out simultaneously using a transition metal catalyst in the presence of an acid selected from the group consisting of: sulphonic acid, sulphuric acid, halogen acid, HY zeolite, lanthanide triflate and triflic acid.

6. A process as claimed in claim 1, wherein steps i) and ii) are carried out simultaneously in the liquid phase, in the presence of an aromatic hydrocarbon solvent.

7. A process as claimed in claim 1, wherein step i) is carried out before step ii).

8. A process as claimed in claim 7, wherein the step i) is carried out in the presence of an acid or a base, and step ii) is carried out in the presence of a transition metal catalyst.

9. A process as claimed in claim 7, wherein step i) is carried out in the presence of an acid selected from the group consisting of: sulphonic acid, sulphuric acid, halogen acid, HY zeolite, lanthanide triflate and triflic acid, and step ii) s carried out in the presence of a transition metal catalyst containing at least one of copper, vanadium, chromium, molybdenum, tungsten, manganese, rhenium, iron, cobalt, nickel, ruthenium, rhodium, palladium, platinum, osmium and/or iridium.

10. A process as claimed in claim 7, wherein step i) carried out in the liquid phase, in the presence of an aromatic hydrocarbon solvent.

11. A process as claimed in claim 1, wherein the n-butenyl ester is produced by reacting butadiene and a carboxylic acid to produce a mixture of sec-butenyl ester and n-butenyl ester.

12. A process as claimed in claim 11, wherein the butadiene is reacted with the carboxylic acid in the presence of a heterogeneous catalyst selected from the group consisting of: Amberlyst 15®, Amberlite IR120®, Nafion®, phosphoric acid functionalised polymers, supported heteropolyacids and HY zeolites.

13. A process as claimed in claim 11, wherein butadiene is reacted with the carboxylic acid in the presence of a homogeneous catalyst selected from the group consisting of sulphonic acids, heteropolyacids, triflic acid and triflate salts.

14. A process as claimed in claim 11, wherein the butadiene employed is in the form of a hydrocarbon stream comprising butadiene.

15. A process as claimed in claim 11, wherein the carboxylic acid is an aliphatic mono-carboxylic acid.

16. A process as claimed in claim 11, wherein the sec-butenyl ester produced by the reaction between the butadiene and the carboxylic acid is converted into methyl ethyl ketone by hydrolysing the sec-butenyl ester to form the corresponding but-1-en-3-ol and ii) isomerising the but-1-en-3-ol produced to form methyl ethyl ketone.

17. A process as claimed in claim 11, wherein the sec-butenyl ester is recycled directly back to the butadiene/carboxylic acid reaction, or converted back into butadiene and carboxylic acid in a separate reaction step.

* * * * *